United States Patent [19]
Bergmann et al.

[11] Patent Number: 5,631,013
[45] Date of Patent: May 20, 1997

US005631013A

[54] COSMETIC DEODORANT PRODUCTS CONTAINING ENCAPSULATED CO-MICRONIZED BICARBONATE INGREDIENT

[75] Inventors: Wolfgang R. Bergmann, Princeton; Richard T. Murphy, Belle Mead, both of N.J.

[73] Assignee: Church & Dwight Co., Inc., Princeton, N.J.

[21] Appl. No.: 511,863

[22] Filed: Aug. 7, 1995

[51] Int. Cl.⁶ ................................................ A61K 7/32
[52] U.S. Cl. .................. 424/401; 424/65; 424/67; 424/484; 424/493; 424/642; 424/717; 424/DIG. 5; 514/777; 514/778; 514/951
[58] Field of Search ........................ 424/401, 484, 424/65, 69, 67, DIG. 5, 493, 642, 717

[56] References Cited

U.S. PATENT DOCUMENTS 5,482,720  1/1996  Murphy et al. .................... 424/489

*Primary Examiner*—Thurman K. Page
*Assistant Examiner*—James M. Spear
*Attorney, Agent, or Firm*—Irving M. Fishman

[57] ABSTRACT

This invention provides cosmetic stick, roll-on and cream deodorant and deodorant-antiperspirant products. The cosmetic products consisting of an organic matrix having a dispersed phase of encapsulated particles of a co-micronized crystallite blend of inorganic compounds such as sodium bicarbonate and zinc oxide. The particle surfaces are coated with a polymer such as maltodextrin starch. When this type of cosmetic product is applied to underarm surfaces, a sustained deodorant activity by the encapsulated particles is obtained.

32 Claims, No Drawings

COSMETIC DEODORANT PRODUCTS CONTAINING ENCAPSULATED CO-MICRONIZED BICARBONATE INGREDIENT

CROSS-REFERENCE TO RELATED APPLICATION

The subject matter of this patent application is related to that disclosed in U.S. patent application Ser. No. 08/320,864, filed Oct. 11, 1994 U.S. Pat. No. 5,482,720; incorporated by reference.

BACKGROUND OF THE INVENTION

Antiperspirants combat axillary odors by inhibiting perspiration through the action of astringent salts such as aluminum and zinc salts, but may be irritating to a large number of users. Deodorants function by neutralizing the objectionable odors resulting from the degradation of several components of perspiration by chemical and microbial action into malodorous fatty acids.

Numerous solid antiperspirant and/or deodorant compositions have been described in the chemical and cosmetic literature. These compositions generally are emulsion sticks or suspensoid sticks. Emulsion sticks contain a solution of the antiperspirant ingredient incorporated into the stick via an emulsion. Although emulsion sticks are desirable in certain respects, they tend to be unstable, exhibit tackiness, and leave a visible residue on the skin after use. Suspensoid sticks contain the powdered antiperspirant ingredient suspended in the stick without the use of water or an emulsion. While suspensoids have stability, they tend to leave a white chalky residue on the skin after application.

Manufacturers have found that anhydrous antiperspirant stick systems are more marketable and have good consumer acceptance primarily due to the ease of application to the skin, good cosmetic esthetics and an acceptable degree of effectiveness. Previous to the development of anhydrous stick systems, numerous water based systems were developed in which the active astringent salts were solubilized in a thickened or gelled composition. This is exemplified in U.S. Pat. Nos. 2,732,327; 2,857,315; 3,255,082; and 3,928,557. The water based systems are difficult to apply to the skin, and their consistency and effectiveness are variable.

Many anhydrous stick compositions have been described in the literature which attempt to improve the delivery and the effectiveness of their antiperspirant and deodorant characteristics. Antiperspirant stick systems consisting of low molecular weight monohydric alcohols in conjunction with polyhydric alcohols are described in U.S. Pat. No. 4,137,306. These sticks have the advantage of quicker drying rates, but the residue of the polyhydric alcohols in combination with the astringent salts produces a high degree of tack, and their effectiveness is limited to the type and amount of astringent salts that could be incorporated in the stick matrix.

Anhydrous stick compositions that suspend the aluminum salt in a hydrophobic matrix are described in U.S. Pat. No. 4,049,792. These compositions employ waxy materials and long chain fatty esters to form a stick that delivers the active astringent salts to the skin.

Cosmetic stick compositions made in accordance with these embodiments are greasy, and the active astringent salt is enveloped in a manner that prevents maximum performance. To alleviate this inherent negative characteristic, volatile silicone fluids replacement of the less volatile long chain fatty esters is described in U.S. Pat. No. 4,126,679. This disclosure teaches the advantage of utilizing a volatile non-staining liquid such as cyclic dimethylpolysiloxanes (referred to as volatile silicones), in combination with various types of waxes, as a carrier for the active astringent salts in an antiperspirant stick composition. Similar antiperspirant stick compositions containing volatile silicones are described in U.S. Pat. Nos. 4,511,554; 4,980,156; and 4,985,238.

With respect to deodorant activity, sodium bicarbonate has long been recognized for its deodorant properties, and has commonly been used as a household deodorant. Plain powdered sodium bicarbonate, or sodium bicarbonate diluted with talc or other filler, has been used as an underarm deodorant as disclosed in U.S. Pat. No. 4,382,079. Other publications which describe cosmetic stick compositions containing a bicarbonate deodorant include U.S. Pat. No. 4,822,602 and U.S. Pat. No. 4,832,945.

However, the development of a practical and effective antiperspirant composition in cosmetic stick form which is also capable of deodorization, and which is capable of consumer acceptability, presents many factors which are unique. Because sodium and potassium bicarbonate have only limited solubility in water, alcohol and other solvents, the preparation of a composition suitable for dispensing in cosmetic stick form has involved many processing obstacles. In addition to the problem of limited solubility, sodium bicarbonate often is incompatible with the active astringent salts and with other ingredients of conventional stick compositions. Also, the dimensional stability of the cosmetic stick containing sodium bicarbonate, and the esthetic appearance and the "feel" on the skin, are just a few of the additional difficulties encountered in the preparation of a low residue cosmetic deodorant or antiperspirant-deodorant product. The high density of a suspended particle-phase of bicarbonate ingredient relative to the low density of an organic matrix phase contributes to the instability and settling of the bicarbonate particle phase in a cosmetic stick, roll-on or cream personal care product.

There is continuing interest in the development of improved cosmetic products which exhibit deodorant activity, or antiperspirant-deodorant activity.

Accordingly, it is an object of this invention to provide a cosmetic stick roll-on or cream product which exhibits deodorant properties, and is characterized by excellent esthetics and cosmetic properties.

It is another object of this invention to provide a homogeneous cosmetic deodorant product which contains a dispersed phase of particulate deodorant ingredient in an organic matrix phase.

It is another object of this invention to provide a homogeneous deodorant product which contains a dispersed particle phase of polymer-encapsulated co-micronized bicarbonate salt crystallites, and which is dimensionally stable.

Other objects and advantages of the present invention shall become apparent from the accompanying description and examples.

DESCRIPTION OF THE INVENTION

One or more objects of the present invention are accomplished by the provision of an encapsulated co-micronized bicarbonate salt powder composition comprising (1) discrete crystallite particles of at least one ingredient selected from alkali metal and ammonium bicarbonates, and (2) between about 10–50 weight percent of discrete crystallite particles of at least one inorganic compound ingredient having a Mohs hardness value between about 3–7; wherein the crystallites of the powder composition have an average particle size in the range between about 0.1–30 microns as obtained by mill co-micronization of the powder ingredients; and wherein the crystallites are in the form of polymer surface-coated particles.

The co-micronized bicarbonate salt and inorganic compound crystallites typically can have an average particle size between about 1–20 microns. The crystallites in their polymer surface-coated form can have an average particle size between about 10–80 microns.

A present invention polymer-encapsulated crystallite composition typically is free-flowing and essentially free of agglomerated solids. A polymer surface-coated particle can have a core matrix of a single crystallite, or it can have a core matrix of multiple crystallites, such as between about 2–10 crystallites.

The term "discrete" as employed herein refers to particles which are individually distinct solids.

In another embodiment this invention provides a process for producing an encapsulated co-micronized bicarbonate salt powder composition which comprises (1) blending ingredients comprising (a) at least one crystalline compound selected from alkali metal and ammonium bicarbonates, and (b) between about 10–50 weight percent of at least one crystalline inorganic compound having a Mohs hardness value between about 3–7; (2) milling the blend to co-micronize the ingredients to discrete crystallite particles having an average particle size in the range between about 0.1–30 microns; and (3) coating the crystallite particle surfaces with a polymer.

A blend of co-micronized crystallite particles is produced in step(2), and the particles characteristically are in an unagglomerated form, and the step(3) product is a blend of encapsulated crystallite particles which has free-flow properties.

The bicarbonate salt starting material of an invention co-micronized powder composition is selected from alkali metal and ammonium bicarbonates, such as sodium bicarbonate, potassium bicarbonate and ammonium bicarbonate, and mixtures thereof. The bicarbonate salt starting material before co-micronization typically has an average particle size in the range between about 40–600 microns.

The inorganic compound starting material is at least one compound having a Mohs hardness value between about 3–7. The inorganic compound is higher than the 2–3.5 Mohs hardness value of the alkali metal or ammonium bicarbonate ingredient.

Inorganic normally have an average Mohs value of about 3–4, inorganic silicates have an average Mohs value of about 5–6, and inorganic oxides have an average Mohs value of about 5–7.

Suitable inorganic compounds for purposes of the present invention compositions include calcium carbonate, copper carbonate, zinc carbonate, barium carbonate, magnesium carbonate, manganese carbonate, calcium silicate, magnesium silicate, copper silicate, manganese silicate, titanium dioxide, tin oxide, zinc oxide, silicon oxide, aluminum oxide, magnesium oxide, copper oxide, zirconium oxide, beryllium oxide, calcium fluoride, zinc sulfide, aluminum phosphate, and the like.

A blend of co-micronized crystallite particles obtained from step(2) of the invention process exhibits novel properties which are derived from the particular method of preparation, i.e., a crystalline bicarbonate salt compound is mill co-micronized with a crystalline inorganic compound having a Mohs hardness value between about 3–7.

If an alkali metal or ammonium bicarbonate salt as a sole ingredient is subjected to a mill micronization procedure, the resultant ultrafine powder tends to be in the form of cohesive agglomerated crystallites of primary particles, and the powder is not free-flowing.

The presence of a crystalline compound ingredient during a co-micronization procedure in step(2) of the invention process provides at least two advantages.

First, the crystalline inorganic compound ingredient serves as a grinding medium because of its particle hardness, and the average size of the bicarbonate salt particles is reduced into an ultrafine micron range.

Second, the presence of the crystallite crystalline inorganic compound particles in a co-micronized powder composition inhibits agglomeration of the ultrafine bicarbonate salt particles, and the co-micronized powder is free-flowing.

In step(2) of the invention process, the co-micronized bicarbonate salt blend of crystallite particles can be prepared by means of a grinding, impact or fluid energy type of milling equipment which is designed to micronize crystalline solids to ultrafine powders.

One type of mill involves the use of rollers or balls in combination with an annular grinding plate, such as bowl roll mills, roller mills and ring-ball mills. Another type of mill involves the use of a pulverizing rotor. These types of mills are illustrated in U.S. Pat. Nos. 2,253,839; 4,550,879; 4,562,972; 4,566,639; 4,919,341; and references cited therein.

Fluid energy jet mills have found application for the comminution of a wide variety of particulate solids. Jet mills are well adapted to micronize and particle size classify particulate solids into ultrafine powders. An important application is the micronization of pigments such as titanium dioxide.

Fluid energy jet mills are size reduction machines in which particles to be ground are accelerated in a stream of gas, (e.g., compressed air) and micronized in a grinding chamber by their impact against each other or against a stationary surface in the grinding chamber. Different types of fluid energy mills can be categorized by their particular mode of operation. Mills may be distinguished by the location of feed particles with respect to incoming air. In the commercially available Majac jet pulverizer (Majac Inc.), particles are mixed with the incoming gas before introduction into the grinding chamber. In the Majac mill, two streams of mixed particles and gas are directed against each other within the grinding chamber to cause fracture. An alternative to the Majac mill configuration is to accelerate within the grinding chamber particles that are introduced from another source, such as a mill with an annular grinding chamber into which numerous gas jets inject pressurized air tangentially (U.S. Pat. No. 3,565,348).

During jet mill grinding, particles that have reached the desired size are separated, while the remaining coarser particles continue to be ground. The particle size classification process can be accomplished by the circulation of the gas and particle mixture in the grinding chamber. In pancake type mills, the gas is introduced around the periphery of the cylindrical grinding chamber to induce a vorticular flow within the chamber. Coarser particles tend to the periphery where they are ground further, while finer particles migrate to the center of the chamber where they are drawn off into a collector outlet located in proximity to the grinding chamber.

Particle size classification can also be accomplished by a separate classifier. This type of classifier is mechanical and features a rotating vaned cylindrical rotor. The air flow from the grinding chamber only can force particles below a certain size through the rotor against the centrifugal forces imposed by the rotor's speed. These particles are the mill's micronized product. Oversized particles are returned to the grinding chamber.

Variation in fluid energy jet mill design are illustrated in U.S. Pat. Nos. 4,219,164; 4,261,521; 4,280,664; 4,526,324; 4,602,743; 4,638,953; 4,664,319; 4,811,907; 4,880,169; 4,962,893; 4,133,504; and references cited therein.

The application of the polymer coating to the blend of co-micronized crystallite particles in step(3) of the invention process is accomplished by conventional means such as pan coating, fluidized coating, centrifugal fluidized coating, and the like. The coating polymer usually is dissolved in a suitable solvent such as water, methanol, ethanol, acetone, tetrahydrofuran, ethyl acetate, dimethylformamide, and the like, as appropriate for a selected polymer species. A coating polymer also can be applied in the form of an emulsion or suspension. After the coating medium is applied to the particles, the solvent medium is removed by evaporation, thereby forming a continuous film coating which encapsulates the discrete crystallite particles.

The coating thickness on the crystallite surfaces typically will vary in the range between about 0.1–20 microns. The coating can consist of a single layer or multiple layers. The polymeric coating can constitute between about 5–50 weight percent of the total dry weight of the coated particles.

A polymer employed for coating the crystallite particles in step(3) of the invention process is selected from hydrophilic organic polymers and hydrophobic (water-insoluble) organic polymers and mixtures thereof.

A hydrophilic polymer employed for coating the crystallite particles is selected from water-soluble and water-dispersible organic polymers. A mixture of polymers can be employed, and a content of between about 0.5–40 weight percent of a water-insoluble polymer, based on the coating weight, can be included with a hydrophilic polymer.

The term "hydrophilic" as employed herein refers to an organic polymer which has a water-solubility of at least about one gram per 100 grams of water at 25° C. The term "hydrophobic" or "water-insoluble" as employed herein refers to an organic polymer which has a water solubility of less than about one gram per 100 grams of water at 25° C.

Suitable hydrophilic polymers for coating co-micronized crystallite particles include gum arabic, gum karaya, gum tragacanth, guar gum, locust bean gum, xanthan gum, carrageenan, alginate salt, casein, dextran, pectin, agar, sorbitol, 2-hydroxyethyl starch, 2-aminoethyl starch, maltodextrin, amylodextrin, 2-hydroxyethyl cellulose, methyl cellulose, carboxymethyl cellulose salt, cellulose sulfate salt, polyvinylpyrrolidone, polyethylene glycol, polypropylene glycol, polyethylene oxide, polyvinyl alcohol/acetate, and the like. Polyvinyl acetate is illustrative of a water-insoluble polymer which can be included as an additional coating component to moderate the hydrophilicity of a hydrophilic polymer coating.

Suitable water-insoluble polymers, alone or in combination with one or more other components, for coating co-micronized crystallite particles include polyvinyl acetate, polyacrylamide, polyvinyl chloride, polystyrene, polyethylene, polyurethane, and the like.

For purposes of release of the core matrix crystallites of bicarbonate salt or inorganic compound in the encapsulated particles when introduced into an aqueous environment, a surface coating of water-insoluble polymer preferably has a content between about 5–30 weight percent of a particulate water-extractable organic or inorganic filler, such as sodium bicarbonate, sodium carbonate, sodium chloride, calcium chloride, monosaccharide or disaccharide, sorbitol, mannitol, and the like.

The rate of release of bicarbonate salt or inorganic compound core matrix crystallite content of the encapsulated particles under moisture conditions can be controlled by the quantity and type of polymer coating on the particle surfaces.

Low molecular weight hydrophilic polymers will release the particle core matrix content at a relatively fast rate in the presence of moisture. High molecular weight polymers which are less hydrophilic will release at a relatively slow rate. Additional rate control is obtained by employing mixtures of polymer components of varied hydrophilicity.

Polyethylene glycol (M.W. of 4000) or polyvinyl alcohol will release the particle core matrix content at a relatively fast rate. Polyethylene oxide (M.W. of 4,000,000) or partially hydrolyzed polyvinyl acetate will release at a relatively slow rate. Polyvinylpyrrolidone will release the particle core matrix content at an immediate rate, when the encapsulated particles are in contact with an underarm type of moisture as an ingredient of a cosmetic stick, roll-on or cream personal care product.

A present invention encapsulated co-micronized bicarbonate salt powder composition exhibits a unique combination of properties because of the novel physical form of the free-flowing polymer-coated particles when utilized as an ingredient in personal care and specialty type products.

The inclusion of a present invention encapsulated co-micronized bicarbonate salt powder as an ingredient enhances odor absorption and neutralization in personal care products, such as those adapted for skin care, oral care or feminine hygiene usage.

A present invention encapsulated co-micronized bicarbonate salt powder as an ingredient provides improved esthetics in creams, lotions, gels, ointments, soapbars, toothpastes, and the like. Irritation is minimized, skin mildness is improved, and antibacterial/antifungal activity is increased.

Another valuable property of a present invention encapsulated co-micronized bicarbonate salt powder composition is an exceptional capability to blend readily into suspension formulations with other ingredients. The ultrafine size and polymer-coated surface area of the co-micronized crystallites facilitate the formation of a homogeneous solid-phase suspension in an organic medium which has long term stability.

Other advantages are achieved by the utility of a present invention encapsulated powder composition. As noted in the Background section of the specification, the relative densities of liquid and solid phases in a cosmetic stick, roll-on or cream personal care product directly affects the stability and esthetics of the formulations. Density matching of inorganic and organic phases is a significant factor in cosmetic stick roll-on and cream products. The present invention provides an encapsulated co-micronized bicarbonate salt powder deodorant ingredient of lower density which more closely matches the density of the organic matrix of a cosmetic stick, roll-on or cream product than does uncoated bicarbonate ingredient.

When there is density matching of organic matrix and dispersed hydrophilic polymer-coated bicarbonate particle phases, a cosmetic stick, roll-on or cream product has improved dimensional stability, and better esthetic appearance and "feel" when applied to human skin.

In another embodiment this invention provides a cosmetic deodorant product comprising a liquid, semi-solid or solid organic matrix which contains between about 0.5–20 weight percent, based on the product weight, of an encapsulated co-micronized bicarbonate salt powder composition homogeneously dispersed therein, wherein the encapsulated power composition comprises (1) discrete crystallite particles of at least one ingredient selected from alkali metal and ammonium bicarbonates, and (2) between about 10–50 weight percent of discrete crystallite particles of at least one inorganic compound ingredient having a Mohs hardness value between about 3–7, based on the powder composition weight; wherein the crystallites of the powder composition have an average particle size in the range between about 0.1–30 microns as obtained by mill co-micronization of the powder ingredients; and wherein the crystallites are in the form of polymer surface-coated particles.

A present invention cosmetic stick, roll-on or cream deodorant product can contain between about 5–25 weight percent of an antiperspirant compound as an additional ingredient.

A present invention cosmetic stick product can consist of a solid organic matrix comprising the following parts by weight of ingredients:

| | |
|---|---|
| volatile oil | 10–55 |
| liquid emollient | 1–35 |
| low melting point wax | 12–30 |

The solid organic matrix has homogeneously dispersed therein between about 0.5–20 weight percent, based on the product weight, of a polymer-encapsulated co-micronized powder composition as described hereinabove.

An invention antiperspirant-deodorant cosmetic stick product typically contains the following weight proportions of main ingredients:

| Ingredient | Weight |
|---|---|
| volatile oil | 25–50 |
| liquid emollient | 2–20 |
| wax (MP 95°–180° F.) | 15–20 |
| antiperspirant | 20–28 |
| encapsulated co-micronized bicarbonate powder | 0.1–25 |
| surfactant | 1–3 |

The volatile oil ingredient preferably is selected from silicone and branched-chain hydrocarbon compounds.

A volatile silicone oil ingredient in a cosmetic stick or roll-on product of the present invention preferably is a cyclic or linear polydimethylsiloxane containing between about 3–9 silicon atoms. A suitable cyclic volatile polydimethylsiloxane compound is illustrated by the formula:

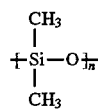

wherein n is an integer with a value of about 3–7.

A suitable linear polydimethylsiloxane is illustrated by the formula:

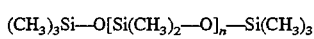

where n is an integer with a value of about 1–7.

Linear volatile silicone compounds generally have viscosities of less than about 5 centistokes at 25° C., while the cyclic type compounds have viscosities of less than about 10 centistokes.

Typical of the volatile silicone compounds that can be employed for purposes of the present invention is cyclomethicone, which is a cyclic dimethylpolysiloxane conforming to the above formula where n averages between 3–6. Dow Corning 245 Fluid (Dow Corning) is a cyclic volatile silicone which is commercially available. CTFA Cosmetic Ingredient Dictionary, Third Edition, (Estrin et al., Editors; The Cosmetic, Toiletry and Fragrance Association, Inc.; 1982) lists cyclic silicones on page 60, under the entry "Cyclomethicone".

A volatile hydrocarbon oil type of ingredient preferably is a $C_{12}$–$C_{20}$ branched-chain hydrocarbon compound or mixture. Suitable volatile branched-chain hydrocarbon oils include isododecane ($C_{12}$), isohexadecane ($C_{16}$), isoeicosane ($C_{20}$), and the like. These types of branched-chain hydrocarbons are marketed by Permethyl Corporation under tradenames such as Permethyl 99A, Parmethyl 101A and Permethyl 102A.

The liquid emollient ingredient of an invention cosmetic stick or roll-on product is selected from one or more water-insoluble organic compounds which are liquid at 25° C. and which contribute a combination of properties that are advantageous in an invention cosmetic stick or roll-on product.

The term "water-insoluble" as employed herein refers to an emollient ingredient which has a water-solubility of less than about one gram per 100 grams of water at 25° C.

A present invention emollient ingredient exhibits a low degree of irritation and toxicity in topical applications, and provides a softening or soothing effect on surface skin tissue.

Preferred water-insoluble liquid emollients include fatty acids such as oleic and ricinoleic; fatty alcohols such as oleyl, lauryl and hexadecyl; esters such as diisopropyl adipate, benzoic acid esters of $C_9$–$C_{15}$ alcohols, and isononyl isononanoate; alkanes such as mineral oil; silicones such as dimethylpolysiloxane and cyclic dimethylpolysiloxane; and ethers such as polyoxypropylene butyl ether and polyoxypropylene cetyl ether. Preferred water-insoluble liquid emollients include diisopropyl adipate, 2-ethylhexyl palmitate, dimethylpolysiloxane (50 cst.), and polyoxypropylene (14) butyl ether.

The low melting point wax ingredient of a present invention cosmetic stick product comprises one or more organic compounds which have a melting point in the range between about 95°–180° F.

Suitable types of wax-like compounds include fatty acids, fatty alcohols, fatty acid esters, fatty acid amides, and the like, which have an aliphatic chain length between about 8–30 carbon atoms. Illustrative of wax-like compounds are cetyl alcohol, palmitic acid, myristyl alcohol, stearyl alcohol, paraffin, and the like, and mixtures thereof.

The low melting point wax ingredient can include up to about 30 weight percent, based on the weight of wax ingredient, of a wax which has a melting point between about 180°–220° F. Illustrative of these higher melting waxes are beeswax, spermaceti, carnauba, bayberry, candelilla, montan, ozokerite, ceresin, paraffin, castor wax, Fischer-Tropsch waxes, and the like.

The antiperspirant ingredient of a present invention cosmetic stick or roll-on product typically is a particulate astringent compound which has an average particle size between about 1–100 microns. Superior cosmetic stick properties are obtained if part or all of the antiperspirant ingredient is in the form of particles which have a diameter less than about one micron. Optionally, the antiperspirant ingredient can be pre-coated with a polymer to prevent interaction with the other ingredients, and to provide a sustained-release antiperspirant activity under application conditions.

Suitable astringent compounds include aluminum chloride, aluminum chlorohydrate, aluminum sulfocarbolate, aluminum sulfate, aluminum-zirconium chlorohydrate, zinc sulfate, zinc sulfocarbolate, and zirconium chlorohydrate. Preferred types of astringent compounds are aluminum chlorohydrates and aluminum-zirconium chlorohydrates, such as aluminum-zirconium trichlorohydrex glycine. Aluminum-zirconium tetrachlorohydrex glycine is commercially available as Rezal 36 GP Superultrafine (Reheis), and Reach AZP 908 (Reheis).

Optional ingredients also may be included in an invention cosmetic formulation, such as bacteriostats, fungistats, fillers, stabilizing agents, antioxidants, pigments, coloring agents, perfumes, chelating agents, and the like.

A surfactant ingredient of an invention cosmetic formulation is selected from nonionic, cationic and anionic polymers. Suitable surfactant polymers include cetyltrimethylammonium bromide; sodium lauryl sulfate; sodium dodecylbenzenesulfonate; ammonium lignosulfonate; condensation products of ethylene oxide with fatty alcohols, amines or alkylphenols; partial esters of fatty acids and hexitol anhydrides; polyalkylene glycol esters; and the like. Illustrative of a preferred type of surfactant polymer is polyethylene glycol (PEG) stearate, which is commercially available as PEG 600 distearate.

A bacteriostat such as 2,4,4'-trichloro-2'-hydroxydiphenyl ether (Triclosan) typically is added in a quantity between about 0.08–3 weight percent, based on the weight of the cosmetic stick, roll-on or cream product.

In another embodiment this invention provides a cosmetic roll-on product consisting of a liquid organic matrix comprising the following parts by weight of ingredients:

| Volatile oil | 55–70 |
|---|---|
| liquid emollient | 3–10 | and the liquid organic matrix has homogeneously dispersed therein about 0.5–20 parts by weight, based on the product weight, of a polymer-encapsulated co-micronized powder composition as described hereinabove.

In general, the ingredients of a cosmetic formulation can be blended in any order. However, in the practice of the invention process for cosmetic stick manufacture there is advantage in utilizing a phased order of ingredient addition and blending under controlled temperature conditions. Additional advantage is obtained in the invention process if there is a minimal time lapse between the alkali metal bicarbonate deodorant ingredient addition step and the cosmetic stick container filling and solidifying step. Alkali metal bicarbonate can convert to alkali metal carbonate, carbon dioxide and water at elevated temperatures.

Adding the encapsulated co-micronized bicarbonate salt powder as the last ingredient of the blended formulation, and processing the formulation to the solid cosmetic stick formation stage within a short time period, are factors which minimize the degradation of the bicarbonate salt ingredient, and the undesirable formation of water and carbon dioxide vapor byproducts. The addition and mixing of the co-micronized bicarbonate salt ingredient into the formulation, and the dispensing of the formulation into cosmetic stick containers, can be accomplished as an essentially instantaneous procedure by utilizing an integrated mixing valve nozzle device, such as the type described in U.S. Pat. Nos. 2,816,518; 3,454,198; 3,949,904; 4,318,429; 4,549,813; 5,046,538; 5,094,276; and the like.

The practice of the invention process for the production of a cosmetic stick product can be conducted in conventional equipment, and is readily adaptable to a commercial-scale manufacturing operation.

The hardness of a present invention cosmetic stick can have a value which varies in the range between about 2.0–8.0, and preferably is in the range between about 2.3–3.3.

The penetration values (in millimeters) of the cosmetic stick products described herein are measured with a Universal Penetrometer, Model TS-73510 AN-2 (Precision Scientific Inc.).

The penetration values are obtained by following a standardized procedure in accordance with ASTM Method D217–94.

A present invention antiperspirant-deodorant cosmetic stick, roll-on or cream product has exceptional properties for treating or preventing perspiration and malodor associated with human underarm perspiration. A present invention cosmetic formulation can be applied effectively with safety and comfort for reduction of underarm perspiration and offensive odors.

The following Examples are further illustrative of the present invention. The components and specific ingredients are presented as being typical and various modifications can be derived in view of the foregoing disclosure within the scope of the invention.

EXAMPLE I

This Example illustrates the preparation of a present invention co-micronized sodium bicarbonate/zinc oxide composition by air-jet milling.

Air-jet pulverized sodium bicarbonate is commercially available (Particle Size Technology, Inc.). The commercial sodium bicarbonate has an average particle size of about 5 microns, and 90 percent of the particles have a diameter less than 20 microns. The sodium bicarbonate is substantially in the form of crystallites of agglomerated primary particles which are not free-flowing.

In accordance with the present invention, air-jet milling equipment (similar to that in U.S. Pat. No. 4,880,169) is employed to prepare a free-flowing co-micronized composition consisting of 70 weight percent of sodium bicarbonate and 30 weight percent of zinc oxide. The co-micronized composition has an average particle size of about 20 microns. The co-micronized composition is unagglomerated and free-flowing.

The sodium bicarbonate starting material has an average particle size of about 50 microns. The zinc oxide starting material has an average particle size of about 10 microns, and a Mohs hardness value of about 4.

The procedure described above is repeated, except that magnesium oxide is substituted for the zinc oxide. The magnesium oxide has a Mohs hardness value of about 6. The sodium bicarbonate/magnesium oxide powder is substantially unagglomerated and free-flowing.

If sodium bicarbonate alone is jet-milled following the above-described procedure, an agglomerated product is obtained which is not free-flowing.

EXAMPLE II

This Example illustrates a fluidized bed procedure for coating a co-micronized mixture of bicarbonate salt and crystalline inorganic compound with a hydrophilic polymer in accordance with the present invention.

A fluidized bed vessel is utilized which is equipped with a Wurster air-suspension coater system (WARF) as described in U.S. Pat. No. 4,568,559 and U.S. Pat. No. 4,877,621.

A coating solution is prepared by dissolving polyethylene glycol (45 g, Poly-G 2000, Olin Corp.), and propylene glycol butyl ether (10 g, PPG 14, Americol) in ethanol (500 g)/water (75 g).

A co-micronized powder of sodium bicarbonate and zinc oxide prepared by the method illustrated in Example I is utilized as the core matrix discrete particles. The co-micronized powder is charged into the coating chamber of the coater system.

Compressed air is introduced into the coating chamber, and the polymeric coating solution is sprayed on the air-suspended co-micronized core matrix particles, until the coating weight is about 30% of the total dry weight of the coated particles.

The procedure is repeated, except that Hydroxypropylmethylcellulose (Methocel 60 HG, Dow Chemical Co.) is employed as the hydrophilic polymer.

The procedure is repeated, except that multodextrin (Lodex 10; Durkee Foods) or amylodextrin is employed as the water-soluble polymer, and 0.5 g of a surfactant is included in the solution (polyoxyethylenesorbitan monolaurate; Tween 20; ICI Americas, Inc.).

The procedure is repeated except that a co-micronized mixture of discrete potassium bicarbonate and zinc oxide particles are employed as the encapsulated core matrix.

The above described procedures produce encapsulated co-micronized bicarbonate salt powder compositions which have an average particle size between about 22–35 microns.

EXAMPLE III

This Example illustrates a procedure for the preparation of an antiperspirant-deodorant cosmetic stick product in accordance with the present invention.

A stainless steel tank is provided which is equipped with turbine agitation. Silicone oil DC 245 (400 lbs, Dow Corning) and Dow DC 200 (37.50 lbs, Dow Corning) are charged to the mixing tank. Agitation (55–65 RPM) is initiated, and heating the liquid medium to 176° F. is commenced.

During the heating period, the following ingredients are added to the stirred liquid medium:

|  | lbs. |
|---|---|
| Lanette 18 DEO[1] | 175.00 |
| Castorwax MP-80[2] | 31.25 |
| ICI G-2162[3] | 6.25 |

[1]Stearyl alcohol; Henkel.
[2]Hydrogenated castor oil; RTD.
[3]PEG 25 PG stearate; ICI.

The mixture is stirred at 176° F. for about 30 minutes until the ingredients are melted and the liquid medium is homogeneous. The stirring speed is reduced to about 35 RPM, then Cyprus Supra A Talc 1625 (18.75 lbs, Cyprus) and Reach AZP 908 aluminum-zirconium tetrachlorohydrex glycine (312.50 lbs, Reheis) are added. The temperature is maintained at 176° F. for about 40 minutes until the fluid medium is uniform, and then the temperature is lowered to 154° F.

Encapsulated co-micronized sodium bicarbonate/zinc oxide (70/30; 140 lbs.) and Sobica F41 fragrance (6.25 lbs, Takasago) respectively are added with stirring to Silicone oil DC 245 (200 lbs, Dow Corning) in a second mixing tank at a temperature of 154° F. to form a homogeneous suspension medium. The sodium bicarbonate/zinc oxide particles are pre-coated with amylodextrin following the procedure described in Example II. The encapsulated particles have an average particle size of about 30 microns.

The contents of the two mixing tanks which contain heated fluid medium are transferred to separate fill tanks through a Greer mill, and the fill tanks are connected to a mixing and dispensing nozzle device, of the type described in U.S. Pat. No. 5,094,276. The nozzle device is adapted for homogeneously blending the two separate streams of fluid media, and dispensing a predetermined quantity of the blended fluid.

Plastek 2 oz. bottom-fill stick containers are filled with the blended fluid. The container contents are cooled to a room temperature solid stick over a period of about 45 minutes. The average hardness value of the solid sticks is 2.8 (ASTM Method D217–94).

A second deodorant cosmetic stick product is prepared by eliminating the antiperspirant ingredient, and increasing the quantity of co-micronized sodium bicarbonate/zinc oxide ingredient from 140 lbs to 250 lbs in the above described manufacturing process.

EXAMPLE IV

This Example illustrates the preparation of an antiperspirant-deodorant roll-on product in accordance with the present invention.

A roll-on formulation is prepared by blending the following proportions of ingredients:

|  | lbs. |
|---|---|
| Silicone oil DC 245 | 60.90 |
| Quaternium-18 hectorite clay (Rheox) | 10.00 |
| Reach AZP 908 | 23.00 |
| Encapsulated potassium bicarbonate/zinc oxide (80/20)[1] | 5.00 |
| Cab-o-Sil fumed silica (Cabot) | 0.60 |
| Sobica | 0.50 |

[1]Discrete particles are precoated with amylodextrin following the procedure described in Example II. The encapsulated particles have an average particle size of about 36 microns.

The roll-on formulation exhibits excellent dimensional stability when packaged and maintained under storage conditions for six months.

EXAMPLE V

This Example illustrates the preparation of a deodorant cream product in accordance with the present invention.

|  | lbs. |
|---|---|
| Cyclomethicone D-5[1] | 36.0 |
| Light mineral oil[2] | 10.0 |
| Permethyl 101A[3] | 10.0 |
| Encapsulated potassium bicarbonate/zinc oxide | 30.0 |

-continued

|  | lbs. |
| --- | --- |
| (80/20)[4] | |
| Propylene carbonate | 1.5 |
| Quaternium-18 hectorite | 6.0 |
| Castor wax | 4.5 |

[1] Cyclic polydimethylsiloxane (G.E. Silicones).
[2] Benol white mineral oil (Witco).
[3] Branched chain hydrocarbon fluid (Permethyl Corp.).
[4] Example IV preparation.

All of the ingredients are combined and heated to 70° C. with agitation. The admixture is cooled to 45° C., and milled with a Tekmar mill to form a stiff cream.

The cream product is applied to underarm skin surfaces, and it reduces the level of perceived odor, and provides a soothing effect.

What is claimed is:

1. A cosmetic deodorant product comprising an organic matrix which contains between about 0.5–20 weight percent of an encapsulated powder composition homogeneously dispersed therein, wherein the encapsulated powder composition comprises (1) discrete crystallite particles of at least one ingredient selected from alkali metal and ammonium bicarbonates, and (2) between about 10–50 weight percent of discrete crystallite particles of at least one inorganic compound ingredient having a Mohs hardness value between about 3–7, based on the powder composition weight; wherein the crystallites of the powder composition have an average particle size in the range between about 0.1–30 microns as obtained by mill co-micronization of the powder ingredients; and wherein the crystallites are in the form of polymer surface-coated particles.

2. A cosmetic deodorant product in accordance with claim 1 which is a cosmetic stick, roll-on or cream formulation.

3. A cosmetic deodorant product in accordance with claim 1 wherein the average crystallite size in the polymer-encapsulated particles is in the range between about 1–20 microns.

4. A cosmetic deodorant product in accordance with claim 1 wherein the polymer-encapsulated particles contain multiple crystallites.

5. A cosmetic deodorant product in accordance with claim 1 wherein the inorganic compound ingredient in the co-micronized powder is selected from metal oxides, carbonates, silicates, phosphates and sulfides.

6. A cosmetic deodorant product in accordance with claim 1 wherein the polymer-encapsulated crystallites comprise sodium bicarbonate and zinc oxide.

7. A cosmetic deodorant product in accordance with claim 1 wherein the polymer-encapsulated crystallites comprise potassium bicarbonate and zinc oxide.

8. A cosmetic stick product consisting of a solid organic matrix comprising the following parts by weight of ingredients:

| volatile oil | 10–55 |
| --- | --- |
| liquid emollient | 1–35 |
| low melting point wax | 12–30 | and the solid organic matrix contains between about 0.5–20 weight percent, based on the product weight, of a polymer-encapsulated co-micronized powder composition homogeneously dispersed therein, wherein the encapsulated powder composition comprises (1) discrete crystallite particles of at least one ingredient selected from alkali metal and ammonium bicarbonates, and (2) between about 10–50 weight percent of discrete crystallite particles of at least one inorganic compound ingredient having a Mohs hardness value between about 3–7, based on the powder composition weight; wherein the crystallites of the powder composition have an average particle size in the range between about 0.1–30 microns as obtained by mill co-micronization of the powder ingredients; and wherein the crystallites are in the form of polymer surface-coated particles.

9. A cosmetic stick product in accordance with claim 8 wherein the volatile oil ingredient comprises a cyclic or linear polydimethylsiloxane containing 3–9 silicon atoms.

10. A cosmetic stick product in accordance with claim 8 wherein the volatile oil ingredient comprises a $C_{12}$–$C_{20}$ branched-chain hydrocarbon.

11. A cosmetic stick product in accordance with claim 8 wherein the liquid emollient ingredient is a water-insoluble organic acid, ester or ether compound.

12. A cosmetic stick product in accordance with claim 8 wherein the wax ingredient is selected from $C_8$–$C_{30}$ alcohol, acid, ester and amide compounds.

13. A cosmetic stick product in accordance with claim 8 wherein the inorganic compound ingredient in the co-micronized powder is selected from metal oxides, carbonates, silicates, phosphates and sulfides.

14. A cosmetic stick product in accordance with claim 8 wherein the polymer-encapsulated crystallites comprise sodium bicarbonate and zinc oxide.

15. A cosmetic stick product in accordance with claim 8 wherein the polymer-encapsulated crystallites comprise potassium bicarbonate and zinc oxide.

16. A cosmetic stick product in accordance with claim 8 wherein the polymer surface-coating on the particles comprises between about 5–50 weight percent of the dry particle weight.

17. A cosmetic stick product in accordance with claim 8 wherein the surface-coating on the particles is a hydrophilic polymer or a water-insoluble polymer or a mixture thereof.

18. A cosmetic stick product in accordance with claim 8 wherein the surface-coating on the particles is a polysaccharide compound.

19. A cosmetic stick product in accordance with claim 8 wherein the surface-coating on the particles is a hydrocolloid.

20. A cosmetic stick product in accordance with claim 3 wherein the surface-coating on the particles is a starch compound.

21. A cosmetic stick product in accordance with claim 8 wherein the surface coating on the particles is multodextrin or amylodextrin or a mixture thereof.

22. A cosmetic stick product in accordance with claim 8 wherein the surface-coating on the particles is a hydrophilic polymer having a content between about 0.5–40 weight percent of a water-insoluble polymer, based on the coating weight.

23. A cosmetic stick product in accordance with claim 8 which has a content between about 0.05–10 weight percent of a biocidal ingredient.

24. A cosmetic stick product in accordance with claim 8 which contains between about 5–25 weight percent of an antiperspirant compound as an additional ingredient.

25. A cosmetic roll-on product consisting of a liquid organic matrix comprising the following parts by weight of ingredients:

| | |
|---|---|
| volatile oil | 55–70 |
| liquid emollient | 3–10 | and the liquid organic matrix contains between about 0.5–20 weight percent, based on the product weight, of a polymer-encapsulated composition homogeneously dispersed therein, wherein the encapsulated powder composition comprises (1) discrete crystallite particles of at least one ingredient selected from alkali metal and ammonium bicarbonates, and (2) between about 10–50 weight percent of discrete crystallite particles of at least one inorganic compound ingredient having a Mohs hardness value between about 3–7, based on the powder composition weight; wherein the crystallites of the powder composition have an average particle size in the range between about 0.1–30 microns as obtained by mill co-micronization of the powder ingredients; and wherein the crystallites are in the form of polymer surface-coated particles.

26. A cosmetic roll-on product in accordance with claim 25 wherein the inorganic compound ingredient in the co-micronized powder is selected from metal oxides, carbonates, silicates, phosphates and sulfides.

27. A cosmetic stick product in accordance with claim 8 wherein the polymer-encapsulated crystallites comprise sodium bicarbonate and zinc oxide.

28. A cosmetic stick product in accordance with claim 8 wherein the polymer-encapsulated crystallites comprise potassium bicarbonate and zinc oxide.

29. A cosmetic stick product in accordance with claim 8 which has a content between about 0.05–10 weight percent of a biocidal ingredient.

30. A cosmetic stick product in accordance with claim 8 which contains between about 5–25 weight percent of an antiperspirant compound as an additional ingredient.

31. A method of practicing personal hygiene which comprises applying a claim 1 cosmetic deodorant product to underarm surfaces in a deodorant-effective amount.

32. A method in accordance with claim 31 wherein the deodorant product is a cosmetic stick, roll-on or cream formulation.

* * * * *